US009028867B2

(12) United States Patent
Narasaki et al.

(10) Patent No.: US 9,028,867 B2
(45) Date of Patent: May 12, 2015

(54) FORMULATION HAVING ACCURATE DOSE-DIVIDING FUNCTION (75) Inventors: Masahiko Narasaki, Yamaguchi (JP); Tomoya Akutagawa, Yamaguchi (JP); Reiko Oku, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 1763 days.

(21) Appl. No.: 12/063,721

(22) PCT Filed: Aug. 17, 2006

(86) PCT No.: PCT/JP2006/316542
§ 371 (c)(1),
(2), (4) Date: May 20, 2008

(87) PCT Pub. No.: WO2007/021032
PCT Pub. Date: Feb. 22, 2007

(65) Prior Publication Data
US 2009/0110726 A1 Apr. 30, 2009

(30) Foreign Application Priority Data
Aug. 18, 2005 (JP) .................................. 2005-237369

(51) Int. Cl.
*A61K 9/20* (2006.01)

(52) U.S. Cl.
CPC ............. *A61K 9/2072* (2013.01); *A61K 9/2054* (2013.01); *A61K 9/2059* (2013.01); *A61K 9/2077* (2013.01); *A61K 9/2086* (2013.01)

(58) Field of Classification Search
None
See application file for complete search history.

(56) References Cited

U.S. PATENT DOCUMENTS

| 4,215,104 | A | * | 7/1980 | Ullman et al. | ................. | 424/467 |
| 5,520,929 | A | | 5/1996 | Makino et al. | | |
| 2004/0113319 | A1 | * | 6/2004 | Kondo et al. | ................. | 264/319 |

FOREIGN PATENT DOCUMENTS

| CN | 1437531 A | 8/2003 |
| EP | 1 437 116 A1 | 7/2004 |
| JP | 36017099 | 6/1960 |
| JP | 49050126 A | 9/1972 |
| JP | 6-9375 A | 1/1994 |
| JP | 8-53345 A | 2/1996 |
| JP | 09-104619 A | 4/1997 |
| JP | 11-1425 A | 1/1999 |
| JP | 2001-72579 A | 3/2001 |
| JP | 2004-189703 A | 7/2004 |
| WO | 00/18447 A2 | 4/2000 |
| WO | 2003/026560 A1 | 4/2003 |
| WO | 03/051339 A1 | 6/2003 |
| WO | WO 2005112900 A1 * | 12/2005 |

OTHER PUBLICATIONS

Japanese Office Action dated Jul. 19, 2011, as issued in Japanese Patent Application No. 2007-531052.
Australian Office Action dated Dec. 15, 2011, as isued in Australian Patent Application No. 2011235987.
Australian Office Action dated Dec. 24, 2010, as issued in Australian Patent Application No. 2006280656.
Japanese Office Action dated Apr. 12, 2011, as issued in Japanese Patent Application No. 2007-531052.
Ozeki, et al., Development of Dividable One-Step Dry-Coated Tablets (Dividable-OSDRC) and Their Evaluation as a New Platform for Controlled Drug Release, Pharmaceutical Research, vol. 21, No. 7, Jul. 2004, (©2004), pp. 1177-1183.
European Search report issued on May 2, 2012 in Application No. 06796705.9-2112.
Canadian Office Action issued in application No. 2619744 dated Mar. 22, 2013.

* cited by examiner

*Primary Examiner* — Ernst V Arnold
(74) *Attorney, Agent, or Firm* — Sughrue Mion, PLLC (57) ABSTRACT

The present invention provides a tablet comprising a plurality of drug-containing parts and at least one connecting part adhered to the drug-containing parts, and having a scored line capable of dividing the whole tablet on the connecting part; particularly, a coated tablet in which a connecting part and a coating layer have the same or different drug release controlling functions; a tablet having an insoluble coating on a drug-containing part having a scored line, wherein the drug-containing part has a structure or composition such that the drug is substantially released after the tablet is divided along the scored line and then ingested; and a tablet comprising a plurality of drug-containing parts and at least one connecting part adhered to the drug-containing parts, wherein at least two drug-containing parts have different compositions.
In addition, the present invention provides a method of manufacturing a tablet, wherein a column comprising a plurality of columnar pharmaceutical composition layers having the same cross-section and laminated in the axial direction of the column is compression molded and then compression molded in a direction different from the axial direction of the column.

7 Claims, 5 Drawing Sheets

FORMULATION HAVING ACCURATE DOSE-DIVIDING FUNCTION

CROSS REFERENCE TO RELATED APPLICATIONS

This application is a National Stage of International Application No. PCT/JP2006/316542 filed on Aug. 17, 2006, claiming priority based on Japanese Patent Application No. 2005-237369, filed Aug. 18, 2005, the contents of all of which are incorporated herein by reference in their entirety.

FIELD OF THE INVENTION

The present invention relates to a tablet capable of accurately dividing the amount of a drug, a tablet whose property is changed by division, a tablet retaining a masking function thereof even after division, a tablet stably retaining a plurality of drugs having poor compatibility with each other, and a tablet having a child proof function, and a method of manufacturing these tablets.

BACKGROUND ART

A scored tablet, which is divided by a pharmacist or a patient depending on a dose, optimizes dose control, and improves flexibility upon prescription (For example, see Japanese Patent Laid-open Publication No. H09-104619, U.S. Pat. No. 5,520,929). It is difficult, however, to always divide a tablet equally, in which a drug is dispersed homogenously over the entire tablet, only by providing a scored line, and errors of dose pose a problem. When a healthy individual divides such a conventional scored tablet accurately by an accurate procedure, any of the fragments contains an accurate amount of a drug. No method has been devised, however, to reduce human errors that occur when patients with various diseases and medical staff handle these conventional scored tablets, under various environment of actual medical practice.

In addition, scored tablets in which a plurality of cores containing an active ingredient are disposed, so-called dry-coated tablets, have been known for accurate dose division (see, for example, WO2003/026560; WO2003/051339; and Pharmaceutical Research, Vol. 21, No. 7, July 2004, p 1177-1183).

Since the manufacturing process of dry-coated tablets is complicated to lead to a large loss and the manufacturing speed may not be increased, there has been a problem that the manufacturing cost becomes high.

These dry-coated tablets in that part of or whole core is embedded in an outer layer differ from those of the present invention which does not require an outer layer.

At the same time, some active ingredients of pharmaceutical preparations have unpleasant odor and/or taste depending on their type, and film coating is sometimes applied to mask them (see, for example, Japanese Patent Laid-open Publication No. H08-53345). Further, film coating may be applied to stabilize active ingredients that are unstable to light, water, moisture, or body components such as gastric fluid with which the active ingredients come into contact after taken. Moreover, tablets film-coated to impart a specific function, such as to secure enteric dissolution. However, these functional preparations have a problem of losing the functions by division.

Further, although it is frequently convenient for patients that one tablet contains a plurality of drugs, but some drugs have poor compatibility with others so that they may not be made into a combined drug.

DISCLOSURE OF THE INVENTION

A first object of the present invention is to provide a scored tablet capable of accurately dividing the amount of a drug.

A second object of the present invention is to provide a coated scored tablet with which a drug release controlling function that is the same as that before division may be maintained even after division, or a coated scored tablet with which a drug release controlling function changes after division.

A third object of the present invention is to provide a tablet that may stably retain a plurality of drugs having poor compatibility with each other in one tablet.

A fourth object of the present invention is to provide a tablet that does not exert drug efficacy and ensures safety when ingested erroneously by a person, such as a child and a patient with dementia but exerts drug efficacy when divided by a person who has a certain level of intelligence or higher.

A fifth object of the present invention is to provide a method of manufacturing tablets achieving the above objects.

These problems may be solved by the present inventions as described below.

The first aspect of the present invention is a tablet comprising a plurality of drug-containing parts that optionally contain a pharmaceutical additive and at least one connecting part that connects the drug-containing parts and contains a pharmaceutically acceptable ingredient and optionally a drug, wherein the connecting part has one scored line that may divide the whole tablet. In other words, the tablet is such that each of the drug-containing parts contains the same or different drug, the content of the drug in each of the drug-containing parts is the same or different, and a plurality of fragments each containing the same or different drug at the same or different content may be thus obtained when the tablet is divided along the scored line.

The second aspect of the present invention is, among the tablets according to the first aspect of the present invention, a coated tablet in which the connecting part and a coating layer have the same or different drug release controlling function.

The third aspect of the present invention is a tablet comprising a plurality of drug-containing parts that optionally contain a pharmaceutical additive and at least one connecting part that connects the drug-containing parts and contains a pharmaceutically acceptable ingredient and optionally a drug, wherein at least two drug-containing parts have different compositions.

The fourth aspect of the present invention is a tablet having an insoluble coating on a drug-containing part having a scored line, wherein the drug-containing part has such a structure or composition that a drug is substantially released when the tablet is divided along the scored line and then ingested.

The fifth aspect of the present invention is a method of manufacturing a tablet, wherein a column composed of a plurality of columnar pharmaceutical composition layers having the same cross-section and laminated in the axial direction of the column is compression molded (first molding step), and then compression molded in a direction different from the axial direction of the column (second molding step).

BEST MODE OF CARRYING OUT THE INVENTION

The first aspect of the present invention is a tablet comprising a plurality of drug-containing parts that optionally a pharmaceutical additive and at least one connecting part that connects the drug-containing parts and contains a pharmaceutically acceptable ingredient and optionally a drug, wherein the connecting part has one scored line that may divide the whole tablet. In other words, the tablet is such that each of the drug-containing parts contains the same or different drug, the content of the drug in each of the drug-containing parts is the same or different, and a plurality of fragments each containing the same or different drug at the same or different content may be thus obtained when the tablet is divided along the scored line. The tablet according to the first aspect of the present invention may be coated entirely.

The size of the tablet according to the first aspect of the present invention is not particularly limited, as long as the tablet is not inappropriately small to be divided as a scored tablet and is not inconveniently large to be taken as a tablet. The thickness is neither limited, as long as division is not prevented. The shape is neither particularly limited, as long as the tablet may be manufactured without difficulty using an ordinary manufacturing apparatus or a modified manufacturing apparatus thereof, and a typical example is a disk that is a general concept of a tablet. Although other typical examples include lower height of triangular and hexagonal columns and a rectangular parallelepiped, its shape is not particularly concerned, as long as the basic functions of the respective parts described below are not spoiled.

The shape of the connecting part is desirably such that the upper and lower surfaces are basically planar. However, there may be a rise and a fall or a concave and a convex, as long as the shape may retain the drug-containing parts and the shape does not interfere with cutting only along the scored line.

One connecting part has one scored line. Although the scored line is also expressed as a splitting groove, "scored line" is named generically, including a splitting groove, in the present specification. Provision of a scored line on a tablet and general shapes thereof have already been common technical knowledge in this art. Accordingly, the shape of the scored line in the present invention is not particularly limited, as long as it allows patients, pharmacists and the like to divide a whole tablet without difficulty, and the scored line may be easily formed based on the common technical knowledge by the person skilled in the art. Specifically, the shapes of the scored line disclosed in the above patent documents may be mentioned as examples. For example, when the connecting part has a planar shape, a scored line may be present on both surfaces or a single surface. When the connecting part is columnar, a scored line may be provided on its whole surface.

Although the drug-containing part may be composed of a drug only, an active ingredient, or may also contain a pharmaceutical additive, it forms part of the tablet according to the present invention and must be solid retaining a certain shape. When it contains a pharmaceutical additive, the drug is desirably dispersed homogenously therein.

The drug as an active ingredient is not particularly limited, as long as the drug may be formulated as the tablet of the present invention by a usual manufacturing method. Examples thereof are, one or more active ingredients selected from, for examples, central nervous system drugs, peripheral nervous system drugs, circulatory drugs, gastrointestinal drugs, hormones, urogenital drugs, blood and body fluid drugs, metabolic drugs, antigout drugs, antitumor drugs, antiallergic drugs, bronchodilators, antibiotics, antibacterial drugs, antiviral drugs, wound healing substances, anticonvulsive agents, anticholinergic agents, antihistamines, anti-inflammatory agents, anti-cholesterolemic agents, antihyperlipemic agents, appetite suppressing agents, analeptics, anticoagulants, antiacids, chemotherapeutic agents, nutritional supplements, diagnostic agents, narcotics/psychostimulants, analgesics, antitussive agents, expectoration agents, and the like. More specific examples are one or more active ingredients selected from the group consisting of ascorbic acid, acetaminophen, ethenzamide, ambroxol hydrochloride, alendronate, febuxostat, clenbuterol hydrochloride, ethyl icosapentate, tacalcitol, picosulfate, alfacalcidol, compounds described in Internal Publication No. WO1999/26918, compounds described in International Publication No. WO2001/53291, and compounds described in International Publication No. WO1999/25686, and salts and/or hydrates thereof. The drugs in each of the plurality of drug-containing parts may differ from each other. A combination between a drug(s) in the drug-containing part(s) and a drug in the connecting part when the connecting part contains a drug, is desirably such that no problem occurs upon contact with each other. Typically, the connecting part contains no drug.

Further, a pharmaceutical additive contained in the connecting part and a pharmaceutical additive optionally contained in the drug-containing parts are not particularly limited, as long as they are pharmaceutically acceptable and do not interfere with stable retention of the shape of a tablet. Specifically, for masking a bitter taste, stimulation and the like, crystalline cellulose, lactose, hydroxypropyl cellulose, hydroxypropylmethyl cellulose, partially gelatinized starch, starch, erythritol, mannitol, sorbitol, trehalose, light anhydrous silicic acid or a mixture or granulate thereof is used, and further lubricants, disintegrants, fluidizers, and the like may be also contained to improve manufacturing properties, formability, and preparation functions. In order to maintain or develop an enteric dissolving function, a methacrylic acid copolymer, cellulose acetate phthalate, carboxymethylethyl cellulose, hydroxypropylmethyl cellulose phthalate, hydroxypropylmethyl cellulose acetate succinate, hydroxypropylmethyl cellulose or a mixture thereof to which a plasticizer is added is used. In order to maintain or develop a sustained release function, hydroxyethyl cellulose, ethyl cellulose, hydroxypropylmethyl cellulose phthalate, hydroxypropylmethyl cellulose acetate succinate, a carboxyvinyl polymer or a mixture thereof to which a plasticizer is added is used.

Further, in order to maintain light stability after division, titanium oxide, or the like may be added to the ingredients of the connecting part.

The shape of the drug-containing parts other than that of a connecting surface with the connecting part may be completely free, as long as there is no problem in manufacturing, division along a scored line is not interfered and coating may be applied in the case of coated tablets. For example, the shape is rectangular parallelepiped, hemispheric, or cylindrical. The shapes of the plurality of drug-containing parts need not to coincide.

The number of the drug-containing parts in the tablet according to the first aspect of the present invention is preferably 2 to 6, more preferably 2 to 4, particularly preferably 2. When the two drug-containing parts contain the same kind of drugs, the ratio of the amount of the drug is preferably a ratio expressed by integers, such as 1:1, 1:2, 1:3, or 1:4.

Further, the tablet according to the first aspect of the present invention may have a coating layer. An example of such a coating layer is a layer that has a function to avoid disadvantages for patients caused by contact with a drug in the oral cavity or the esophagus. Such disadvantages for patients include, for example, a bitter taste, stimulation, an adverse drug reaction due to unintended absorption of a drug in the oral cavity and an adverse drug reaction due to dissolution of a drug in the oral cavity or the esophagus. Among them, masking of uncomfortable tastes such as the bitter taste and a uncomfortable odor is a typical example. In addition, coating is provided for the purposes, for example, of provision of an enteric dissolution property or sustained release property, stabilization against water or moisture, stabilization against biological components in the body such as gastric juice or enzymes that a drug encounters after administration, or maintenance of stability against light. For masking of a uncomfortable taste or a uncomfortable odor, for example, hydroxypropyl cellulose, and hydroxypropylmethyl cellulose are used. For provision of an enteric dissolution property, for example, a methacrylic acid copolymer, cellulose acetate phthalate, carboxymethylethyl cellulose, hydroxypropylmethyl cellulose phthalate, hydroxypropylmethyl cellulose acetate succinate, hydroxypropylmethyl cellulose, or a mixture thereof to which a plasticizer is added is used. For provision of a sustained release property, for example, hydroxyethyl cellulose, ethyl cellulose, hydroxypropylmethyl cellulose phthalate, hydroxypropylmethyl cellulose acetate succinate, a carboxyvinyl polymer, or a mixture thereof to which a plasticizer is added is used. For stabilization against moisture or the like, ethyl cellulose, methacrylic acid copolymers, shellac, and polyvinylacetal diethylaminoacetate are used. Further, for stabilization against biological components in the body such as gastric juice or enzymes, pharmaceutical additives having a masking, enteric dissolution, or sustained release function are used alone or in combination, and for light stability, titanium oxide or the like is added to these coating bases. Of course, these are only examples, and the coating layer according to the first aspect of the present invention is not limited thereto. In addition, such a coating layer may be a multilayer of various layers.

Although a certain level of variance occurs unavoidably in the manner of division when a scored tablet is divided along a scored line, the shape of the connecting part may be determined so that a divided face is always in the range of the connecting part in the scored tablet according to the first aspect of the present invention. In addition, the shape of the connecting part of the coated tablet is designed so that the coating layer remains on the connecting part after division to avoid exposure of even part of the drug-containing part after division.

Further, the tablet according to the first aspect of the present invention includes a tablet manufactured by compression molding of a multilayer column composed of columnar drug-containing part layers and the columnar connecting part layer(s) laminated alternatively in the axial direction of the column with the drug-containing part layers disposed at both ends in a direction different from the axial direction of the column; and then preparing a scored line during the compression molding or thereafter. Among all, a tablet having two drug-containing parts manufactured by compression molding of a 3-layer column is preferable.

In other words, in the first step, a multilayer column composed of the drug-containing parts and the connecting part(s) laminated alternatively in the axial direction of the column with the drug-containing parts disposed at both ends is tabletted according to an ordinary method. In other word, in this step, the column is compressed in the axial direction of the column. The shape of the multilayer tablet is typically cylindrical or rectangular parallelepiped, but may be other columnar shapes, as long as there is no problem in manufacturing. Then, in the second step, the multilayer tablet is removed from the tabletting machine, and then subjected to compression molding in a direction different from the direction of the column, preferably from a perpendicular direction to the axial direction of the column using the tabletting machine again. The tabletting in the second step may be performed without removal from the tabletting machine, for example, by appropriate rotations in the tabletting machine, depending on the structure of the tabletting machine. Further, tabletting may be performed without rotating a tablet under molding in the tabletting machine by using a tabletting machine having a tabletting mechanism in two perpendicular directions. A scored line is formed simultaneously with or following the tabletting in the second step. Among all, the manufacturing method in which a column having 3 layers is subjected to compression molding is preferable.

Figure 1:
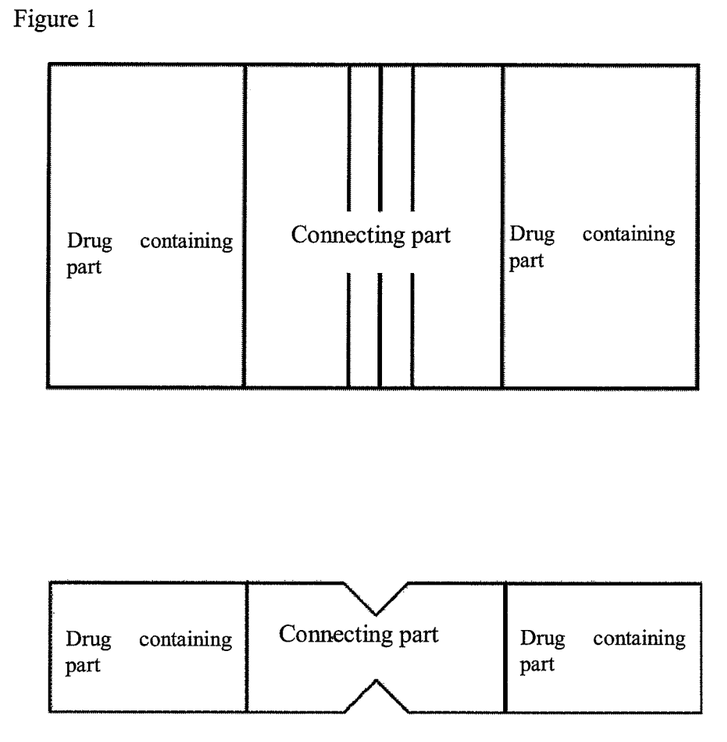
FIG. 1 shows a specific example of the first aspect of the present invention. The upper part is a plain view and the lower part is a side view. A scored line is provided on both surfaces.
Figure 2:
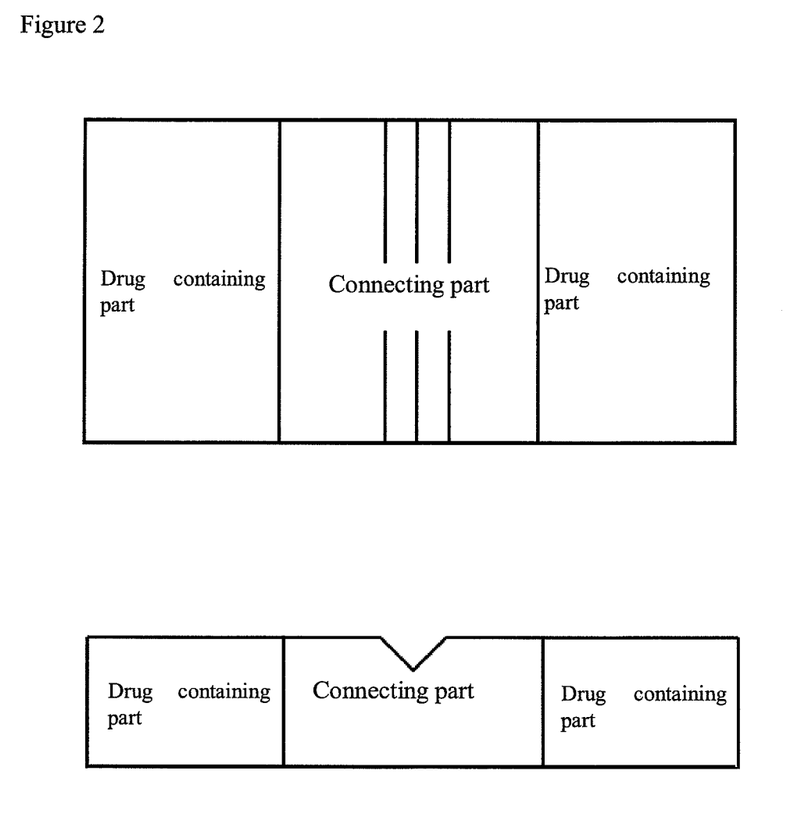
FIG. 2 shows a specific example of the first aspect of the present invention. The upper part is a plain view and the lower part is a side view. A scored line is provided on one surface.
Figure 3:
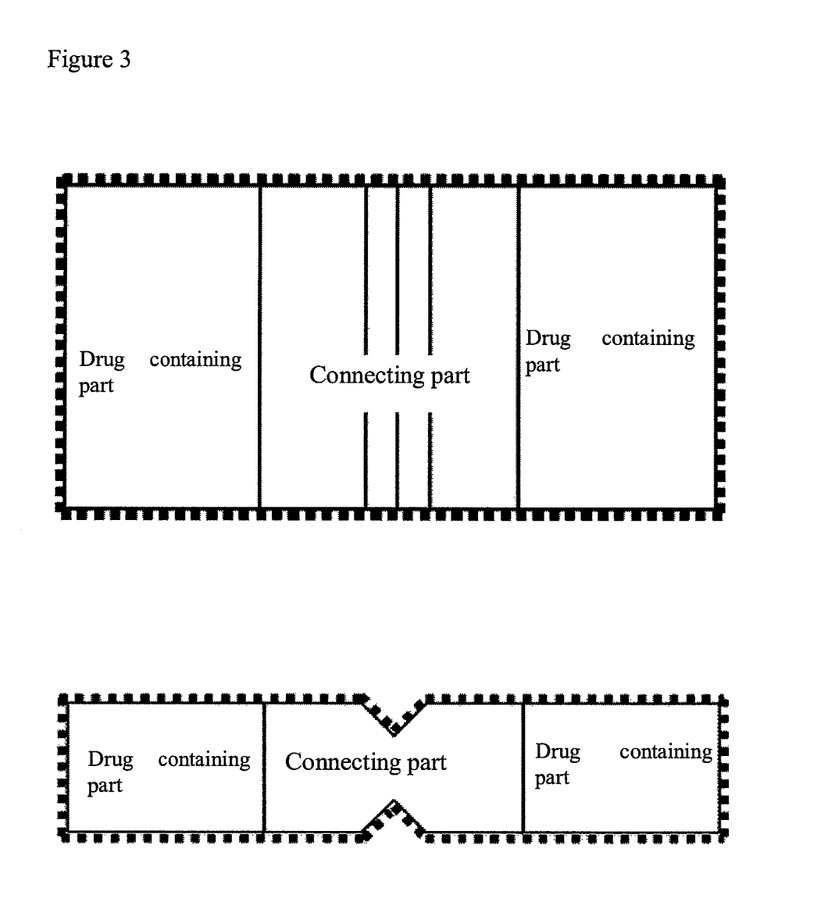
FIG. 3 shows a specific example of the first aspect or the second aspect of the present invention. The upper part is a plain view and the lower part is a side view. The dotted line on the circumference shows a coating layer.
Figure 4:
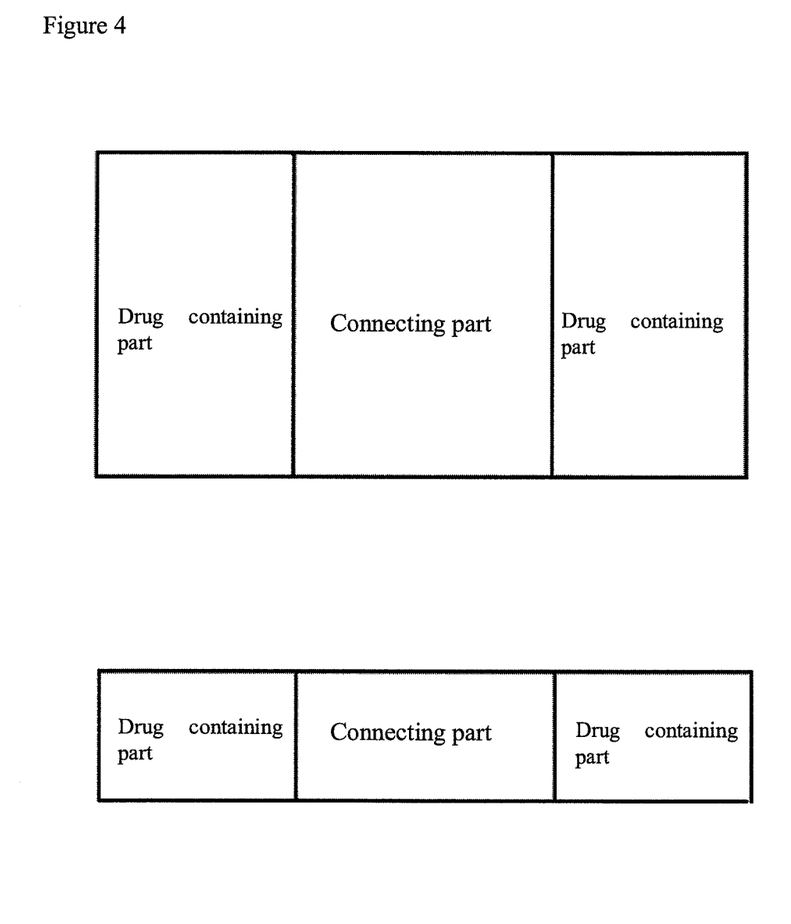
FIG. 4 shows a specific example of the third aspect of the present invention. The upper part is a plain view and the lower part is a side view.
Figure 5:
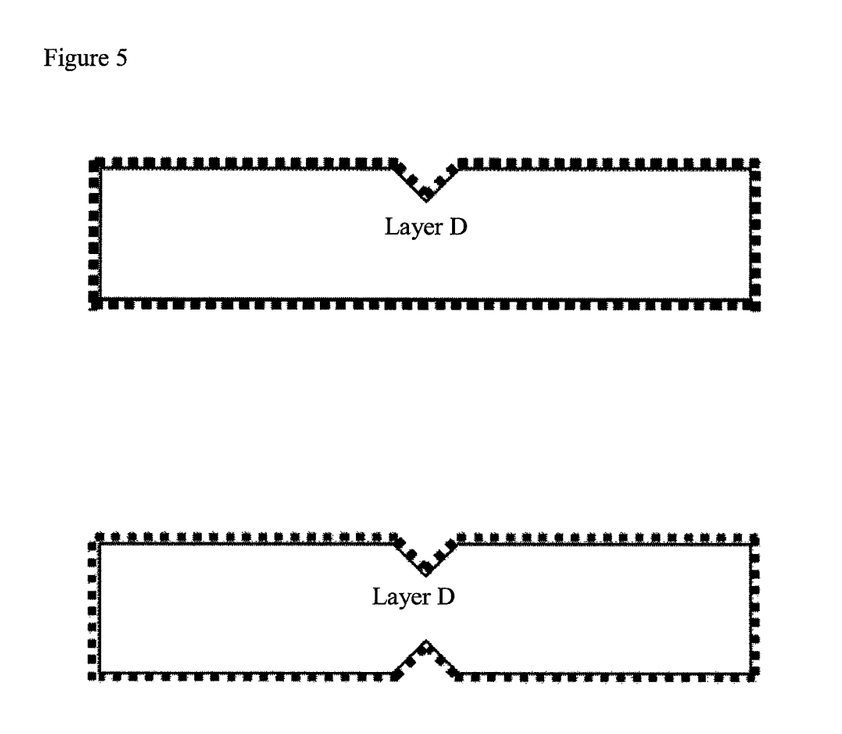
FIG. 5 shows two specific examples of the fourth aspect of the present invention. Layer D has a structure or composition from which a drug is substantially released. The dotted line on the circumference shows a coating layer.

Specific embodiments of the tablet according to the first aspect of the present invention are shown in FIGS. 1 to 3 as examples. Here, the drug-containing part and the connecting part are a rectangular parallelepiped. As described above, however, the shapes of the respective parts and the whole tablet are not limited, as long as the function of the first aspect of the present invention is not impaired. For example, an acute-angled part of the tablet in FIG. 1 may be rounded and the whole tablet may be an elliptical column. Further, although the joining plane between the drug-containing part and the connecting part is planar in FIG. 1, the face may be smoothly curved. Further, as long as the manufacturing may be performed, part of the drug-containing part may be projected into the connecting part or part of the connecting part may be projected into the drug-containing part. The tablet in FIG. 2 differs from the tablet in FIG. 1 in that a scored line is provided only on one surface. Further, the tablet in FIG. 3 differs from the tablet in FIG. 1 in that the tablet has a coating layer shown by a dotted line.

The second aspect of the present invention is, among the first aspect of the present invention, a coated tablet in which the connecting part and the coating layer have the same or different drug release controlling functions. Accordingly, among the above description concerning the first aspect of the present invention, the description concerning the coated tablet is applicable, without modification, to the tablet according to the second aspect of the present invention. Specifically, the description concerning the size and shape of the whole tablet, the shapes of the connecting part and the drug-containing part, the shape of the scored line, a drug as an active ingredient, a pharmaceutical additive contained in the connecting part and a pharmaceutical additive optionally contained in the drug-containing part, a ratio of amounts of a drug in the plurality of the drug-containing parts, and the purpose and the composition of the coating layer is applicable.

Examples of such drug release controlling functions include insolubility, rapid dissolution, rapid disintegration, enteric dissolution, sustained release, and timed-release.

For a tablet whose connecting part and coating layer have the same drug release controlling function, their various functions may be maintained even after division. For example, an enteric dissolution, sustained release, or timed-release function is maintained. In addition, even when the drug release controlling function differs between the connecting part and the coating layer, for example, when the connecting part is composed of an insoluble ingredient and the coating layer functions to avoid disadvantages for patients caused by contact with a drug in the oral cavity or the esophagus, the function of the coating layer is maintained even after the division of tablet. Such disadvantages for patients include, for example, bitter taste, stimulation, adverse drug reactions due to unintended drug absorption in the oral cavity, or adverse drug reactions due to dissolution of a drug in the esophagus. Among these, masking of the bitter taste is a typical example.

At the same time, the tablet according to the second aspect of the present invention in which the connecting part and the coating layer have different drug release controlling functions includes a tablet with which the drug release controlling function changes after a dividing procedure. Examples thereof include a tablet in which the coating layer is an ordinary film coating and the connecting part has a rapid disintegration property; a tablet in which the coating layer is a sustained release coating and the connecting part has a rapid dissolution or timed-release property; a tablet in which the coating layer is an enteric dissolution coating and the connecting part has an insoluble, rapid dissolution, or timed-release property; and a tablet in which the coating layer is a timed-release coating and the connecting part has a rapid dissolution or enteric dissolution property. Here, "ordinary film coating" refers to a water-soluble film coating for the purpose of masking and protection of appearance.

Suitable combinations between the connecting part and the coating layer according to the second aspect of the present invention are shown in the following table. In the table, the mark "–" shows an unsuitable combination, "Δ" means a suitable combination, and "o" means a particularly suitable combination. The terms in the table outline the significance of the combinations.

disintegration property" refers to a state in which disintegration is almost completed within 30 seconds to 1 minute. "Sustained release property" refers to a state in which a certain amount of a main drug ingredient is released at a constant rate within a specified time. "Enteric dissolution property (enteric)" refers to such a function that a drug is not released in the stomach and released after a tablet enters the intestine and pH increases.

In order to make the connecting part to have a rapid dissolution property, as its ingredients, for example, crystalline cellulose, lactose, hydroxypropyl cellulose, hydroxypropylmethyl cellulose, partially gelatinized starch, starch, light anhydrous silicic acid, or a mixture or granulate thereof is used in a mixture of croscarmellose sodium, croscarmellose calcium, starch, partially gelatinized starch, and the like as disintegrants. In order to impart a disintegration property, disintegrants such as croscarmellose sodium, croscarmellose calcium, partially gelatinized starch, starch, and the like may be added to excipients.

The third aspect of the present invention comprises a plurality of drug-containing parts that optionally contain a pharmaceutical additive and at least one connecting part that connects the drug-containing parts and contains a pharmaceutically acceptable ingredient and optionally a drug, wherein at least two drug-containing parts have different compositions. In other words, a scored line is removed from the tablet according to the first aspect of the present invention, and a feature that the at least two drug-containing parts have difference compositions is added. Accordingly, in the third aspect of the present invention, the description stated for the first aspect of the present invention, namely, concerning the size and shape of the whole tablet, the shapes of the connecting part and the drug-containing parts, a drug as an active ingredient, a pharmaceutical additive contained in the connecting part and a pharmaceutical additive optionally contained in the drug-containing parts, a ratio of amounts of a drug in the plurality of the drug-containing parts, and the purpose and the composition of the coating layer is basically applicable. Of course, since the tablet according to the third aspect of the present invention has no scored line and is not

TABLE

|  | Coating layer is a ordinary film coating | Coating layer is insoluble | Coating layer is a sustained release coating | Coating layer is an enteric coating | Coating layer is a timed-release coating |
|---|---|---|---|---|---|
| Connecting part has an insoluble property | o Function maintained | — | o | o | o |
| Connecting part has a rapid dissolution property | Δ | o Child proof | o Sustained release to ordinary | o Enteric dissolution to ordinary | o Timed-release to ordinary |
| Connecting part has a rapid disintegration property | o Ordinary to rapid disintegration | o Child proof | ΔSustained release to rapid disintegration | ΔEnteric dissolution to rapid disintegration | ΔTimed-release to rapid disintegration |
| Connecting part has an enteric dissolution property | — | o Child proof | — | o Enteric dissolution function maintained | o Timed-release to enteric dissolution |
| Connecting part has a sustained release property | — | o Child proof | o Sustained release function maintained | — | ΔTimed-release to sustained release |
| Connecting part has a timed-release property | — | o Child proof | o Sustained release to timed-release Timed-release occurs in a short time | o Enteric dissolution to timed-release Timed-release occurs in a short time | o Timed-release function maintained Timed-release |

"Insoluble" herein used with respect to a coating layer refers to a level that allows sufficient time after inadvertent swallowing to give treatment thereto, and it is envisaged that it takes 2 to 5 hours or longer to dissolve the layer after a tablet enters the gastrointestinal tract. "Rapid dissolution property" means that most disintegration and dissolution usually occur within about 15 to 30 minutes after ingestion since a tablet is composed of ingredients usually used for preparation. "Rapid required to have a structure capable of dividing the whole tablet, the degree of freedom of the tablet shape is higher than that of the tablet according to the first aspect of the present invention.

The effect of the tablet according to the third aspect of the present invention may be summarized as follows:

Firstly, there is an advantage that even when the difference in the composition of the drug-containing parts is a difference in the type of drugs and these drugs are poorly compatible with each other, a combined drug of these drugs is provided.

There is also an advantage that, when different drugs are combined in a tablet and they are poorly compatible due to their additives, a combined drug of these drugs may be provided.

Further, drugs that may be combined as they are in the forms of their original formulation ingredients of the preparations and that are expected to exhibit a synergistic effect may be easily made into a combined drug.

Further, when the contents of the respective drugs largely differ, it is difficult to ensure content uniformity and release properties suitable for the respective drugs using a mixed type. However, in the tablet according to the third aspect of the present invention these properties can be ensured. As described above, even when the combined drug is made of different drugs, the composition of the drug-containing parts may thus be made suitable for the respective drugs.

Examples of such a combined drug include combined drugs containing Mucosolvan and various preparations (specifically, antibiotic preparations, antiallergic preparations, bronchodilator preparations, antitussive expectorant preparations, these drugs may sometimes be poorly compatible); combined drug containing Onealfa and Bonalon (their contents differ largely between μg and mg orders), combined drug containing Mucosolvan and Formoterol, a combined drug containing Mucosolvan and theophylline, a timed-release preparation containing a fibrate drug and HMG-CoA reductase or Onealfa (efficacy is enhanced by simultaneous release) and a combined drug containing Mucosolvan and Mucodyne (having a synergistic effect).

In addition, there is an advantage that even when the release controlling functions of different drugs are different, a combined drug may be made without contamination.

Further, since the process is simple, even for a controlled release preparation containing one drug by combination of rapid release form, sustained release form, and the like, there is an advantage that such processes as coating of core and its embedding position control for a dry-coated tablet are unnecessary. This effect is obtained when the difference in the compositions of the drug-containing parts differ only in release property.

The tablet according to the third aspect of the present invention may be easily manufactured by applying the method of manufacturing described above for the first aspect of the present invention. The step of providing a scored line is not required, however. Accordingly, although the manufacturing method of the tablet according to the third aspect of the present invention is not particularly described in Examples, they may be easily manufactured by adopting a manufacturing method in which a step of providing a scored line is omitted from the methods described in Manufacturing Examples described below for scored tablets.

The fourth aspect of the present invention is a tablet having an insoluble coating on the drug-containing part having a scored line, wherein the tablet has such a structure or composition that, when the drug-containing part is divided along the scored line and taken, the drug is substantially released. Accordingly, although drug efficacy is not exhibited and safety is maintained when a child or the like inadvertently swallows the tablet, its intrinsic drug efficacy is exhibited when the tablet is divided and taken by a person having intelligence of a certain level or higher.

Here, the "drug-containing part" may be composed only of certain drugs or may further contain the above described pharmaceutical additives in addition to the drugs. Further, even when the drug-containing part is entirely homogeneous or has a certain inner structure, any drug-containing parts may be acceptable as long as the drug is substantially released when the tablet is divided along a scored line and taken. For example, in the second aspect of the present invention, a tablet in which the coating layer is insoluble and the connecting part has a rapid dissolution or disintegration property may be mentioned. The degree of insolubility of the coating layer in the fourth aspect of the present invention must be such that, when the tablet is inadvertently swallowed, it is harmless. It depends on harmfulness of the drug to be used.

The fifth aspect of the present invention is a method of manufacturing a tablet characterized in that a column composed of a plurality of columnar pharmaceutical composition layers having the same cross-section and laminated in the axial direction of the column is compression molded (first molding step), and then the column is compression molded in a direction different from the axial direction of the column (second molding step). Here, when a scored line is provided in the second molding step or later, a scored tablet may be manufactured.

Although all of the "pharmaceutical composition layers" is composed of a drug and/or a pharmaceutical additive, the adjacent pharmaceutical composition layers are not the same and differ from each other in terms of at least any of the presence/absence, type, composition or concentration of a drug or a pharmaceutical additive.

Here, the meanings of the "pharmaceutical additive" and "scored line" are as described for the first aspect of the present invention and the like.

The number of the pharmaceutical composition layers is preferably 3 to 5, particularly preferably 3.

The cross-section in "the same cross-section" means a cross-section made by a surface perpendicular to the axial direction of a column.

The shape of the column is not limited, as long as it may be manufactured by a tabletting machine, and typical examples of the shape include cylindrical, elliptic cylindrical, and regular polygon column. Among these, a cylindrical column is preferable.

As the manufacturing method of a mold in the first step, for example, a method in which powdery substances to be the respective pharmaceutical composition layers are laminated in turn and then compression molded by a tabletting machine may be mentioned.

The second molding step is compression molding in a direction different from the axial direction of the column, and preferably in a direction perpendicular to the axial direction of the column.

The second molding step is generally performed by removing the column from the above described tabletting machine and then filling the column in a second tabletting machine for compression molding. The removal step and the filling step may be performed manually or automatically. In addition, when a tabletting machine that allows compression molding in a different direction, for example, in the axial direction of the column and a direction perpendicular to the axial direction is prepared; the fifth aspect of the present invention may be embodied by one tabletting machine.

Further, during the second compression, a scored line may be prepared and the form of the preparation may be freely changed, for example, into an oval tablet, a capulet tablet, or the like, as well.

It has been common technical knowledge that a two-step molding may not provide a molding that may stand up to practical use. This is because, when a powder material that has been once compression molded is subjected to compression molding again, the molding is destroyed once and then compression molded again and such destruction occurs unevenly. According to the fifth aspect of the present invention, however, a tablet that is not practically problematic is unexpectedly obtained.

The manufacturing method according to the fifth aspect of the present invention is suitable for manufacturing a tablet according to the first to third aspects of the present invention. In other words, the tablet according to the first to third aspects of the present invention may be manufactured by matching a plurality of columnar pharmaceutical composition layers to the drug-containing parts or the connecting part in the tablet according to the first to third aspect of the present invention, and laminating the drug-containing parts and the connecting parts alternatively with the drug-containing parts disposed at both ends. In short, the fifth aspect of the present invention is a generalized method of manufacturing the tablet according to the first aspect of the present invention, and the like as described above. Of course, the tablets according to the first to third aspects of the present invention are not limited to those manufactured by this manufacturing method.

Further, a tablet of drugs having difficulties in tabletting, such as due to sticking, may be easily manufactured by using a layer containing no drug or a layer containing a drug at a low concentration as a columnar pharmaceutical composition layer disposed at both ends and a layer containing the drug at a relatively higher concentration as at least one of the other layers. The present invention includes tablets obtained by such a manufacturing method.

The content of a drug may be changed by controlling the amounts of the layer containing no drug or the layer containing a drug at a low concentration, without changing the size of a tablet and formulation proportion of the drug layers.

Further, since the second molding step is a compression molding of the molding from the first step from a lateral side, the surface area is much smaller than powdery material and there is thus an advantage that no or a very minor amount of a lubricant is required to allow tabletting. Even in the drugs being likely to cause tabletting trouble, a decrease in hardness or retardation of dissolution due to incorporation of an excessive amount of a lubricant can be prevented.

Further, there is also an advantage that filling accuracy is enhanced in multilayer tabletting by the first molding step, since the depth of filling may be larger than that of normal multilayer tabletting.

In addition, although a form of a tablet is limited in ordinary single compression molding, further compression molding in a different direction may sometimes allow preparation of a tablet having a variety of shapes.

EXAMPLES

The present invention will be illustrated referring to Examples, but is not limited to these Examples.

Example 1

(Small Tablet Filling Method 1): Filling of Lower Layer→Filling of Small Tablet→Compression Molding→Coating To a tabletting machine (Hata Iron Works Co., Ltd., HT-AP6SSU), an oval-type punch and die set (Fuji Yakuhin Kikai Co., Ltd., F-J0392-1, upper punch with scored line) was mounted. In this die, 80 mg of a mixture of Dilactose R (Freund Corporation) and 0.5% magnesium stearate was charged to use as a lower layer. One R tablet having a diameter of 3 mm and a weight of 15 mg (tablet obtained by compression molding of Dilactose R colored with Blue No. 1 using HPC-L) each was filled at both ends of the major axis of the lower layer and subjected to compression molding. The punch-head space at pre-compression was 1.10 mm and the punch-head space at compression was 0.92 mm and the filling depth was 2.95 mm during compression molding.

This tablet was film-coated using a coater (Hicoater Mini, Freund Corporation). Under the operating conditions of an intake gas temperature at 68 to 74° C., an exhaust temperature at 44 to 50° C., a pan rotation number at 20 to 30 rpm, an atomized air at 60 NL/min and a pattern air at 30 NL/min, 233 g of a coating liquid (6% HPMC TC-5, 0.12% PEG 6000P aqueous solution) was sprayed and then dried.

Example 2

Small Tablet Filling Method 1): Filling of Lower Layer→Filling of Small Tablet→Compression Molding→Coating To a tabletting machine (Hata Iron Works Co., Ltd., HT-AP6SSU), an oval-type punch and die set (Fuji Yakuhin Kikai Co., Ltd., F-J0392-1, upper punch with scored line) was mounted. In this die, 80 mg of a mixture of Dilactose R (Freund Corporation) and 0.5% magnesium stearate was charged to use as a lower layer. One R tablet having a diameter of 3 mm and a weight of 15 mg (tablet obtained by compression molding of sodium ascorbate, magnesium stearate and Dilactose R) each was filled into both ends' of the major axis of the lower layer and subjected to compression molding. The punch-head space at pre-compression was 1.10 mm and the punch head-space at compression was 0.92 mm and the filling depth was 2.95 mm during compression molding.

This tablet was film-coated using a coater (Hicoater Mini, Freund Corporation). Under the operating conditions of an intake gas temperature at 68 to 74° C., an exhaust temperature at 44 to 50° C., a pan rotation number at 20 to 30 rpm, an atomized air at 60 NL/min and a pattern air at 30 NL/min, 233 g of a coating liquid (6% HPMC TC-5, 0.12% PEG 6000P aqueous solution) was sprayed and then dried.

Example 3

(Small Tablet Filling Method 2): Filling of Central Tablet→Filling of Small Tablet→Filling of Central Tablet→Compression Molding→Coating To a tabletting machine (Hata Iron Works Co., Ltd., HT-AP6SSU), an oval-type punch and die set (Fuji Yakuhin Kikai Co., Ltd., F-J0392-1, upper punch with scored line) was mounted. In the center of this die, one R tablet having a diameter of 3 mm and a weight of 45 mg (tablet obtained by mixing Dilactose R and 0.5% magnesium stearate and subjecting to compression molding) was filled in parallel to the minor axis direction. One R tablet having a diameter of 3 mm and a weight of 15 mg (tablet obtained by compression molding of HPC-L and Dilactose R colored with Blue No. 1) was filled in the gap developed in the major axis direction. A tablet that is the same as the tablet filled first was then filled on the first tablet, and a rotation plate was rotated to perform compression molding. The punch head-space at pre-compression was 1.07 mm and the punch head-space at compression was 1.02 mm and the filling depth was 2.95 mm during compression molding.

This tablet was film-coated using a coater (Hicoater Mini, Freund Corporation). Under the operating conditions of an intake gas temperature at 68 to 74° C., an exhaust temperature at 44 to 50° C., a pan rotation number at 20 to 30 rpm, an atomized air at 60 NL/min and a pattern air at 30 NL/min, 233 g of a coating liquid (6% HPMC TC-5, 0.12% PEG 6000P aqueous solution) was sprayed and then dried.

Example 4

(Small Tablet Filling Method 2): Filling of Central Tablet→Filling of Small Tablets→Filling of Central Tablet→Compression Molding→Coating To a tabletting machine (Hata Iron Works Co., Ltd., HT-AP6SSU), an oval-type punch and die set (Fuji Yakuhin Kikai Co., Ltd., F-J0392-1, upper punch with scored line) was mounted. In the center of this die, one R tablet having a diameter of 3 mm and a weight of 45 mg (tablet obtained by compression molding of sodium ascorbate, magnesium stearate and Dilactose R) was filled in parallel to the minor axis direction. One R tablet having a diameter of 3 mm and a weight of 15 mg (tablet obtained by compression molding of Dilactose R colored with Blue No. 1 using HPC-L) was filled in the gap developed in the major axis direction. A tablet that is the same as the tablet filled first was then filled on the first tablet, and a rotation plate was rotated to perform compression molding. The punch head-space at pre-compression was 1.07 mm and the punch head-space at compression was 1.02 mm and the filling depth was 2.95 mm during compression molding.

This tablet was film-coated using a coater (Hicoater Mini, Freund Corporation). Under the operating conditions of an intake gas temperature at 68 to 74° C., an exhaust temperature at 44 to 50° C., a pan rotation number at 20 to 30 rpm, an atomized air at 60 NL/min and a pattern air at 30 NL/min, 233 g of a coating liquid (6% HPMC TC-5, 0.12% PEG 6000P aqueous solution) was sprayed and then dried.

Example 5

(Multilayer Tablet Two-Step Compression Method) Preparation of 3-Layer Tablet→Tabletting the Intermediate Layer in Parallel with the Scored Line To a tabletting machine (Hata Iron Works Co., Ltd., HT-P18), a punch and die set for 6 mm R tablets was mounted to tablet a 3-layer tablet composed of an upper layer of 30 mg, an intermediate layer of 60 mg and a lower layer of 30 mg. Dilactose R blended with 0.5% magnesium stearate was used for the upper layer and the lower layer and Dilactose R colored with Bleu No. 1 using HPC-L and 0.5% magnesium stearate was used for the intermediate layer. The tablet was then tabletted by a tabletting machine (Hata Iron Works Co., Ltd., HT-AP6SS-U) in a manner to butt the intermediate layer to the scored line part of the punch and die set for 8 mm scored tablets.

The tablet was film-coated using a coating machine (High coater mini, Freund Corporation). Under the operating conditions of an intake air temperature at 68 to 74° C., an exhaust temperature at 44 to 50° C., a pan rotation number at 20 to 30 rpm, an atomized air at 60 NL/min and a pattern air at 30 NL/min, 233 g of a coating liquid (6% HPMC TC-5, 0.12% PEG 6000P aqueous solution) was sprayed and then dried.

Example 6

(Multilayer Tablet Two-Step Compression Method) Preparation of 3-Layer Tablet→Tabletting the Intermediate Layer in Parallel with the Scored Line To a tabletting machine (Hata Iron Works Co., Ltd., HT-P18), a punch and die set for 6 mm R tablets was mounted to tablet a 3-layer tablet composed of an upper layer of 30 mg, an intermediate layer of 60 mg, and a lower layer of 30 mg. Dilactose R blended with 0.5% magnesium stearate was used for the upper layer and the lower layer, and Dilactose R blended with sodium ascorbate and 0.5% magnesium stearate was used for the intermediate layer. The tablet was then tabletted by a tabletting machine (Hata Iron Works Co., Ltd., HT-AP6SS-U) in a manner to butt the intermediate layer to the scored line part of the punch and die set for 8 mm scored tablets.

The tablet was film-coated using a coating machine (High coater mini, Freund Corporation). Under the operating conditions of an intake air temperature at 68 to 74° C., an exhaust temperature at 44 to 50° C., a pan rotation number at 20 to 30 rpm, an atomized air at 60 NL/min and a pattern air at 30 NL/min, 233 g of a coating liquid (6% HPMC TC-5, 0.12% PEG 6000P aqueous solution) was sprayed and then was dried.

Example 7

(Multilayer Tablet Two-Step Compression Method) Preparation of 3-Layer Tablet→Tabletting the Intermediate Layer in Parallel with the Scored Line To a tabletting machine (Hata Iron Works Co., Ltd., HT-P18), a punch and die set for 7 mm R tablets was mounted to tablet a 3-layer tablet composed of an upper layer of 50 mg, an intermediate layer of 150 mg, and a lower layer of 50 mg. Dilactose R blended with 0.5% magnesium stearate was used for the upper layer and the lower layer, and Dilactose R colored with Bleu No. 1 using HPC-L and 0.5% magnesium stearate was used for the intermediate layer.

The tablet was then tabletted by a tabletting machine (Hata Iron Works Co., Ltd., HT-AP6SS-U) in a manner to butt the intermediate layer to the scored line part of the punch and die set for 8 mm scored tablets (Fuji Yakuhin Kikai Co., Ltd., F-J0379).

Example 8

(Multilayer Tablet Two-Step Compression Method) Preparation of 3-Layer Tablet→Tabletting the Intermediate Layer in Parallel with the Scored Line To a tabletting machine (Hata Iron Works Co., Ltd., HT-P18), a punch and die set for 7 mm R tablets was mounted to tablet a 3-layer tablet composed of an upper layer of 50 mg, an intermediate layer of 150 mg, and a lower layer of 50 mg. Dilactose R blended with 0.5% magnesium stearate was used for the upper layer and the lower layer, and Dilactose R blended with sodium ascorbate and 0.5% magnesium stearate was used for the intermediate layer.

The tablet was then tabletted by a tabletting machine (Hata Iron Works Co., Ltd., HT-AP6SS-U) in a manner to butt the intermediate layer with the scored line part of the punch and die set for 8 mm scored tablets (Fuji Yakuhin Kikai Co., Ltd., F-J0379).

Example 9

(Multilayer Tablet Two-Step Compression Method) Preparation of 3-Layer Tablet→Tabletting the Intermediate Layer in Parallel with the Scored Line Granules containing sodium ascorbate, lactose, partially gelatinized starch and hydroxypropyl cellulose and granules containing lactose, partially gelatinized starch and hydroxypropyl cellulose were respectively blended with crosscarmellose sodium and magnesium stearate to use as powder for tabletting.

To a tabletting machine (Hata Iron Works Co., Ltd., HT-AP6SS-U), a punch and die set for 4.5 mm 3 R tablets (Fuji Yakuhin Kikai Co., Ltd., H-JTR045) was mounted. The powder for tabletting containing sodium ascorbate was filled in the upper layer and the lower layer so that the upper layer and the lower layer contained 10 mg of sodium ascorbate, respectively, and the powder for tabletting containing no sodium ascorbate was filled in the intermediate layer so that a total weight of the tablet was adjusted to about 125 mg. After filling, a 3-layer tablet was prepared at a punch-head space at pre-compression of 4.16 mm and a punch-head space at compression of 4.12 mm.

To a tabletting machine (Hata Iron Works, Co., Ltd., HT-AP6SS-U), a punch and die set for special oval tablets (Fuji Yakuhin Kikai Co., Ltd., F-J0392-1 B type) was then mounted. The 3-layer tablet obtained was inserted in a transverse direction into the punch and die set so that the intermediate layer butted to the scored line part and tabletting was conducted at a punch-head space at pre-compression of 1.12 mm and a punch-head space at compression of 1.07 mm.

The tablet thus obtained was film-coated using a coating machine (High coater mini, Freund Corporation). Under the operating conditions of an intake air temperature at 68 to 74° C., an exhaust temperature at 44 to 50° C., a pan rotation number at 20 to 30 rpm, an atomized air at 60 NL/min and a pattern air at 30 NL/min, 150 g of a coating liquid (6% HPMC TC-5, 1.2% PEG 6000P aqueous solution) was sprayed and then dried.

Example 10

(Division Part Method) Filling of Active Ingredient Layer→Charge of Division Part→Compression Molding Granules containing sodium ascorbate, lactose, partially gelatinized starch and hydroxypropyl cellulose and granules containing lactose, partially gelatinized starch and hydroxypropyl cellulose were respectively blended with crosscarmellose sodium and magnesium stearate to use as powder for tabletting. The powder for tabletting containing no active ingredient was used to prepare a cylindrical division part having a diameter of 3 mm and a length of 6 mm by compression molding.

To a tabletting machine (Hata Iron Works, Co., Ltd., HT-AP6SS-U), a punch and die set for special oval tablets (Fuji Yakuhin Kikai Co., Ltd., upper punch F-J0375, lower punch F-J0374) was mounted. A 90 mg aliquot of the granule for tabletting containing sodium ascorbate was filled, the division part was inserted in the central part thereof, and compression molding was performed at a punch-head space at pre-compression of 0.88 mm and a punch-head space at compression of 0.83 mm.

The tablet thus obtained was film-coated using a coating machine (High coater mini, Freund Corporation). Under the operating conditions of an intake air temperature at 68 to 74° C., an exhaust temperature at 44 to 50° C., a pan rotation number at 20 to 30 rpm, an atomized air at 60 NL/min and a pattern air at 30 NL/min, 150 g of a coating liquid (6% HPMC TC-5, 1.2% PEG 6000P aqueous solution) was sprayed and then dried.

Example 11

Granules containing sodium ascorbate, lactose, partially gelatinized starch and hydroxypropyl cellulose and granules containing lactose, partially gelatinized starch and hydroxypropyl cellulose were respectively blended with crosscarmellose sodium and magnesium stearate to use as powder for tabletting.

The powder for tabletting containing sodium ascorbate was used to prepare a 3-mm sugar-coated tablet weighing 20 mg. To a tabletting machine (Hata Iron Works, Co., Ltd., HT-AP6SS-U), a punch and die set for special oval tablets (Fuji Yakuhin Kikai Co., Ltd., upper punch F-J0374, lower punch F-J0374) was mounted. A 115 mg aliquot of the powder for tabletting containing no sodium ascorbate was filled in the die, one sugar-coated tablet containing sodium ascorbate each was disposed at both ends of the major axis of the die, and compression molding was performed at a punch-head space at pre-compression of 1.78 mm and a punch-head space at compression of 1.66 mm to integrate.

Example 12

Granules containing sodium ascorbate, lactose, partially gelatinized starch and hydroxypropyl cellulose and granules containing lactose, partially gelatinized starch and hydroxypropyl cellulose were respectively blended with crosscarmellose sodium and magnesium stearate to use as powder for tabletting.

The powder for tabletting containing sodium ascorbate was used to prepare a 4-mm flat tablet weighing 40 mg. To a tabletting machine (Hata Iron Works, Co., Ltd., HT-AP6SS-U), a punch and die set for special oval tablets (Fujiyakuhin Kikai, upper punch F-J0374, lower punch F-J0374) was mounted. A 75 mg aliquot of the powder for tabletting containing no sodium ascorbate was filled in the die, one flat tablet containing sodium ascorbate each was disposed at both ends of the major axis of the die, and compression molding was performed at a punch-head space at pre-compression of 1.57 mm and a punch-head space at compression of 1.45 mm to integrate.

Example 13

(Multilayer Tablet Two-Step Compression Method): Preparation of 3-Layer Tablet→Tabletting the Intermediate Layer in Parallel with the Scored Line Granules containing febuxostat, lactose, partially gelatinized starch and hydroxypropyl cellulose and granules containing lactose, partially gelatinized starch and hydroxypropyl cellulose were respectively blended with crosscarmellose sodium and magnesium stearate to use as powder for tabletting.

To a tabletting machine (Hata Iron Works Co., Ltd., HT-AP6SS-U), a punch and die set for 4.5 mm 3 R tablets (Fuji Yakuhin Kikai Co., Ltd., H-JTR045) was mounted. The powder for tabletting containing febuxostat was filled in the upper layer and the lower layer so that the upper layer and the lower layer contained 10 mg of febuxostat, respectively, and the powder for tabletting containing no febuxostat was filled in the intermediate layer so that a total weight of the tablet was adjusted to about 125 mg. After filling, a 3-layer tablet was prepared by compression at a punch head-space at pre-compression of 4.16 mm and a punch-head space at compression of 4.12 mm.

To a tabletting machine (Hata Iron Works, Co., Ltd., HT-AP6SS-U), a punch and die set for special oval tablets (Fuji Yakuhin Kikai Co., Ltd., F-J0392-1 B type) was then mounted. The 3-layer tablet obtained was inserted in a transverse direction into the die so that the intermediate layer butted to the scored line part, and tabletting was conducted at a punch-head space at pre-compression of 1.12 mm and a punch-head space at compression of 1.07 mm.

The tablet thus obtained was film-coated using a coating machine (High coater mini, Freund Corporation). Under the operating conditions of an intake air temperature at 68 to 74° C., an exhaust temperature at 44 to 50° C., a pan rotation number at 20 to 30 rpm, an atomized air at 60 NL/min and a pattern air at 30 NL/min, 150 g of a coating liquid (6% HPMC TC-5, 1.2% PEG 6000P aqueous solution) was sprayed and then dried.

Example 14

(Division Part Method) Filling of Active Ingredient Layer→Charge of Division Part→Compression Molding Granules containing febuxostat, lactose, partially gelatinized starch and hydroxypropyl cellulose and granules containing lactose, partially gelatinized starch and hydroxypropyl cellulose were respectively blended with crosscarmellose sodium and magnesium stearate to use as powder for tabletting. The powder for tabletting containing no active ingredient was used to prepare a cylindrical division part having a diameter of 3 mm and a length of 6 mm by compression molding.

To a tabletting machine (Hata Iron Works, Co., Ltd., HT-AP6SS-U), a punch and die set for special oval tablets (Fuji Yakuhin Kikai Co., Ltd., upper punch F-J0375, lower punch F-J0374) was mounted. A 90 mg aliquot of the granule for tabletting containing febuxostat was filled, the division part was inserted in the central part thereof, and compression molding was performed at a punch-head space at pre-compression of 0.88 mm and a punch-head space at compression of 0.83 mm.

The tablet thus obtained was film-coated using a coating machine (High coater mini, Freund Corporation). Under the operating conditions of an intake air temperature at 68 to 74° C., an exhaust temperature at 44 to 50° C., a pan rotation number at 20 to 30 rpm, an atomized air at 60 NL/min and a pattern air at 30 NL/min, 150 g of a coating liquid (6% HPMC TC-5, 1.2% PEG 6000P aqueous solution) was sprayed and then dried.

Example 15

Granules containing febuxostat, lactose, partially gelatinized starch and hydroxypropyl cellulose and granules containing lactose, partially gelatinized starch and hydroxypropyl cellulose were respectively blended with crosscarmellose sodium and magnesium stearate to use as powder for tabletting.

The powder for tabletting containing febuxostat was used to prepare a 3-mm sugar-coated tablet weighing 20 mg. To a tabletting machine (Hata Iron Works, Co., Ltd., HT-AP6SS-U), a punch and die set for special oval tablets (Fuji Yakuhin Kikai Co., Ltd., upper punch F-J0374, lower punch F-J0374) was mounted. A 115 mg aliquot of the powder for tabletting containing no febuxostat was filled in the die, one sugar-coated tablet containing febuxostat each was disposed at both ends of the major axis of the die, and compression molding was performed at a punch-head space at pre-compression of 1.78 mm and a punch-head space at compression of 1.66 mm for integration.

Example 16

Granules containing febuxostat, lactose, partially gelatinized starch and hydroxypropyl cellulose and granules containing lactose, partially gelatinized starch and hydroxypropyl cellulose were respectively blended with crosscarmellose sodium and magnesium stearate to use as powder for tabletting.

The powder for tabletting containing febuxostat was used to prepare a 4-mm flat tablet weighing 40 mg. To a tabletting machine (Hata Iron Works, Co., Ltd., HT-AP6SS-U), a punch and die set for special oval tablets (Fuji Yakuhin Kikai Co., Ltd., upper punch F-J0374, lower punch F-J0374) was mounted. A 75 mg aliquot of the powder for tabletting containing no febuxostat was filled in the die, one flat tablet containing febuxostat each was disposed at both ends of the major axis of the die, and compression molding was performed at a punch-head space at pre-compression of 1.57 mm and a punch-head space at compression of 1.45 mm to integrate.

INDUSTRIAL APPLICABILITY

The tablet of the present invention is a pharmaceutical and the present invention is utilized in the manufacturers of pharmaceuticals.

The invention claimed is:

1. A method of manufacturing a tablet, comprising:
   (a) compression molding a column having a plurality of columnar pharmaceutical composition layers having the same cross-section and laminated in the axial direction of the column; and
   (b) compression molding the column in a direction different from the axial direction thereof,
   wherein the entire column is compressed into different shape in the compression molding in (b).

2. The manufacturing method according to claim 1, wherein both ends of the column are a pharmaceutical composition layer containing no drug.

3. A manufacturing method of a tablet, comprising compression molding an entire multilayer column having columnar drug-containing parts and a columnar connecting part(s) laminated alternatively in the axial direction of the column with the drug-containing parts disposed at both ends, in a direction different from the axial direction of the column, wherein the column is compressed into a different shape.

4. The manufacturing method according to claim 3, wherein a scored line is prepared during the compression molding or thereafter, as required.

5. The manufacturing method according to any of claims 1 to 4, wherein the direction different from the axial direction of the column is a direction perpendicular to the axial direction of the column.

6. The manufacturing method according to any of claims 1 to 4, wherein the column to be compression molded is a 3-layer column.

7. A tablet manufactured by the method, according to claim 1.

* * * * *